United States Patent [19]

Franz

[11] 4,115,104

[45] Sep. 19, 1978

[54] DICYANOVINYLHYDRAZONOMALONONITRILES AND THE HERBICIDAL USE THEREOF

[75] Inventor: John E. Franz, Crestwood, Mo.

[73] Assignee: Monsanto Company, St. Louis, Mo.

[21] Appl. No.: 768,137

[22] Filed: Feb. 14, 1977

[51] Int. Cl.$^2$ .................. C07C 120/00; C07C 121/82; C07C 121/78; A01N 9/20
[52] U.S. Cl. ........................................ 71/105; 71/98; 260/465 E
[58] Field of Search ................ 260/465 E; 71/105, 98

[56] References Cited

U.S. PATENT DOCUMENTS

| | | | |
|---|---|---|---|
| 3,914,279 | 10/1975 | Begland | 71/105 X |
| 4,014,917 | 3/1977 | Carter | 260/465 E |

OTHER PUBLICATIONS

Roland et al., C.A., 80, 95838t (1974).
Roland et al., C.A., 81, 135418k (1974).

Primary Examiner—Joseph Paul Brust
Attorney, Agent, or Firm—William T. Black; Donald W. Peterson

[57] ABSTRACT

Dicyanovinylhydrazonomalononitriles are described as well as a process for producing same. These malononitriles are useful as herbicides.

59 Claims, No Drawings

DICYANOVINYLHYDRAZONOMALONONITRILES AND THE HERBICIDAL USE THEREOF

This invention relates to novel dicyanovinylhydrazonomalononitriles having utility as herbicides. This invention further relates to methods for preparing said malononitriles, to herbicidal compositions and to herbicidal methods employing said dicyanovinylhydrazonomalononitriles.

The novel dicyanovinylhydrazonomalononitriles of this invention are represented by the following formula

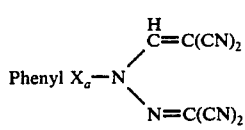
(I)

wherein each X is a substituent on said Phenyl selected from halogen, alkyl of 1 to 8 carbon atoms, alkoxy or alkylthio or haloalkyl of 1 to 8 carbon atoms, cyano or nitro and wherein $a$ is an integer from 0 to 5.

These dicyanovinylhydrazonomalononitriles are produced by the reaction of tetracyanoethylene (TCNE) with a sydnone having the formula

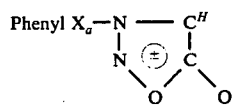
(II)

wherein X and $a$ have the same meanings as in formula I. Preferably, the reaction is conducted with substantially equimolar quantities of the sydnone and the tetracyanoethylene in order to facilitate recovery and purification of the dicyanovinylhydrazonomalononitrile from the reaction mixture. The reaction is not dependent on the use of a catalyst, however, heating of the reaction mixture to temperatures of the order of 160° to 185° C. is required in order to obtain acceptable yields within a reasonable reaction time. The reaction is conducted in the presence of a solvent for the reactants, but which is inert to either reactant and has a boiling point equal to or higher than the reaction temperature. O-dichlorobenzene is a suitable solvent. Other useful inert solvents include p-cymene, mesitylene, benzonitrile and p-chlorotoluene. Conveniently, the reaction can be conducted at atmospheric pressure but higher or lower pressures can be used if desired.

The sydnones represented by formula II, many of which have been described in the literature, are prepared by reacting aniline or an appropriately substituted aniline with ethyl bromoacetate and sodium acetate in ethanol under reflux conditions to yield the corresponding ethyl glycinate which is then hydrolyzed with a base to yield the corresponding N-substituted glycine. The glycine is nitrosated by treatment with sodium nitrite followed by acidification of the basic solution to yield the corresponding N-nitrosoglycine which upon dehydration yields the sydnone. These procedural steps have been described by A. C. Finger, D. R. Dickerson, L. D. Starr and D. E. Orlopp, *J. Org. Chem.*, 30, 405 (1965) and by C. J. Thoman and D. J. Vooden, *Org. Syn., Coll.*, Vol. V, Wiley Interscience Publishers, page 962.

For glycines with strong electron-withdrawing groups on the phenyl ring, the nitrosation is preferably conducted in concentrated hydrochloric acid with addition of sodium nitrite according to the method described by W. Baker, et. al., *J. Chem. Soc.*, 307 (1949). A preferred procedure for dehydrating the N-nitrosoglycines involves reaction of the N-nitrosoglycine with trifluoroacetic anhydride in ether at 0° C. with the desired sydnone precipitating and therefore easily isolated in high yield (W. Baker et. al., *J. Chem. Soc.*, 1542 (1950); H. V. Daeniker et al., *Helv. Chim. Acta*, 40, 918 (1957); and C. J. Fliedner, Jr., *J. Het. Chem.*, 8, 1049 (1971).

The reaction of tetracyanoethylene (TCNE) and a sydnone is believed to proceed initially to form a bicyclic, 1,3 dipolar adduct which immediately upon loss of $CO_2$ transforms to a dicyanovinylhydrazonomalononitrile as schematically illustrated as follows

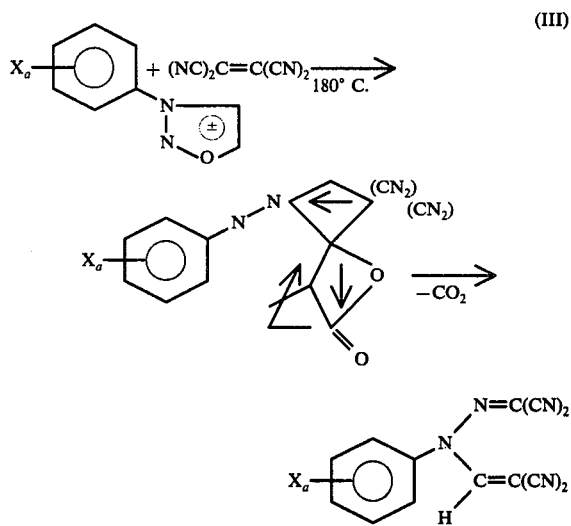
(III)

wherein X and $a$ have the same meanings as in formulas I and II. Confirmation, however, of the existence of the bicyclic, 1,3 dipolar adduct has not yet been forthcoming. It is noteworthy that no pyrazole derivative was produced in this reaction in contrast to the reported pyrazole formation when a sydnone was reacted with a dienophile as in the case of acrylonitrile where cycloaddition with sydnones readily occurred with spontaneous loss of $CO_2$ to produce the corresponding pyrazoles (R. Huisgen et. al, *Chem. Ber.*, 101, 536-551 (1968); H. Gothardt et. al, *Chem. Ber.*, 101, 552-563; Huisgen et. al. *Chem. Ber.*, 101, 829-838 (1968); Huisgen et. al, *Chem. Ber.*, 101, 1059-1071 (1968); K. T. Potts et. al, *Chem. Comm.*, 66, (1969).

General procedure for the reaction of sydnones with TCNE

A mixture of sydnone (0.04 mol), 5.6 g (0.044 mol) of TCNE and 50 ml of o-dichlorobenzene was heated at 165°-170° C. with stirring. After 5-7 hours, the mixture was cooled to room temperature and allowed to remain overnight. The reaction mixture was diluted with 50 ml petroleum ether and filtered. The brown-black residue was washed with petroleum ether and air dried. The solid was then purified by dissolving in hot benzene, treatment with charcoal and boiling the resulting suspension for 10 minutes. After filtration, the benzene was concentrated to one-third volume and petroleum ether added to induce crystallization. The resulting precipitate was then isolated by filtration, washed several times with petroleum ether and dried in the air. The charcoal purification procedure was sometimes repeated if necessary. An analytical sample was prepared by recrystallization from benzene petroleum ether. The following examples serve to further illustrate the invention, all parts being by weight unless otherwise specifically set forth.

EXAMPLE 1

Reaction of N-p-nitrophenyl Sydnone with TCNE

A mixture of the sydnone (1.0 g, 0.0048 mol), TCNE (0.68 g, 0.0053 mol) in o-dichlorobenzene (15 ml) was heated at 168°-170° C. for 7 hours. The cooled solution was treated with TCNE (0.34 g, 0.0026 mol) and heated for 16 additional hours at 168°-170° C. The cooled reaction mixture was diluted with petroleum ether and the solid collected. The material was dissolved in hot benzene, treated with charcoal and the resulting suspension boiled for 10 minutes. After filtration, the benzene solution was concentrated and diluted with petroleum ether. The resulting tan precipitate was isolated, washed with petroleum ether and dried in the air to yield 180 mg (13%), mp 179°-181° C. of alpha-(2-(2,2-dicyanovinyl)-2-(4-nitrophenyl)hydrazono)malononitrile. After recrystallization from benzene-petroleum ether gave a melting point of 185°-187° C. The compound gave the following analysis.

Calc'd.: C: 53.62; H: 1.73; N: 33.67. Found: C: 53.95; H: 1.92; N: 33.11.

EXAMPLE 2

Reaction of N-o-ethylphenyl Sydnone and TCNE

A mixture of the sydnone (1.0 g, 0.0052 mol) and TCNE (0.2 g, 0.0052 mol) in o-dichlorobenzene (11 ml) was heated at 165°-170° C. for 24 hours. To the cooled reaction mixture was added TCNE (0.3 g, 0.002 mol) with 4 ml of o-dichlorobenzene and the mixture was heated at 165°-170° C. for 20 additional hours. The cooled solution was diluted with petroleum ether and the solid collected. The material was taken up in hot benzene, treated with charcoal and the resulting suspension boiled for 10 minutes. After filtration, the solution was concentrated to small volume and petroleum ether added resulting in a tan precipitate. Isolation and drying in the air yielded 160 mg (11%) of the desired alpha-(2-(2,2-dicyanovinyl)-2-(2-ethylphenyl)hydrazono)-malononitrile. Recrystallization from benzene petroleum ether yielded a nearly white solid, mp 172°-174° C. The compound gave the following analysis.

Calc'd.: C: 65.68; H: 3.67. Found: C: 65.94; H: 3.38.

EXAMPLE 3

Reaction of Phenyl Sydnone with TCNE

A mixture of 6.5 g (0.04 mol) of phenyl sydnone, 5.2 g (0.04 mol) of TCNE and 50 ml of o-dichlorobenzene was heated at 170° C. under nitrogen with good agitation. After 3 hours, the mixture was cooled to room temperature and allowed to remain overnight. The reaction mixture was diluted with 50 ml of ether and filtered. The residue was washed with ether and air-dried. The yield of brown powder, mp 181°-182° C., was 7.0 g (71%). The ir spectrum indicated essentially pure alpha-(2-(2,2-dicyanovinyl)-2-phenyl hydrazono)-malononitrile. An analytical sample was prepared by decolorization with charcoal as follows: a mixture of 2 g of crude product, 1 g of decolorizing charcoal and 35 ml of benzene was heated to boiling and the mixture filtered after 1-2 minutes. The residue was extracted with 2-15 ml portions of hot benzene and the combined filtrate allowed to cool. After crystallization was complete, the product was collected and washed with ether. The yield of pure alpha-(2-(2,2-dicyanovinyl)-2-phenyl hydrazono)malononitrile, mp 182.5-184.5, was 1.5 g. From the benzene filtrates there was recovered 0.4 g of additional product with the same ir spectrum; ir (nujol) 3.3 $\mu$ (m), 4.5 $\mu$ (s), 6.2 $\mu$ (s), 6.32 $\mu$ (m), 6.6 $\mu$ (s), 6.9 $\mu$ (m), 7.4 $\mu$ (s), 8.2 $\mu$ (s), 8.42 $\mu$ (s), 8.68 $\mu$ (s), 13.7 $\mu$ (s), 14.4 $\mu$ (s).

Calc'd. for $C_{13}H_6N_6$: C, 63.40; H, 2.46; N, 34.14. Found: C, 62.91; H, 2.43; N, 33.98.

EXAMPLE 4

Reaction of 3-Trifluoromethylphenyl Sydnone with TCNE

A mixture of 9.2 g (0.04 mol) of recrystallized 3-trifluoromethylphenyl sydnone (mp 116°-117° (d), 5.2 g (0.04 mol) of TCNE and 100 ml of o-dichlorobenzene was heated with stirring under nitrogen at the reflux temperature for 7.5 hours. Sublimation of TCNE into the condenser during this period made it difficult to complete the reaction. The reaction mixture was cooled to room temperature and filtered. The residue was washed with benzene and petroleum ether. The air-dried brown-grey solid, mp 179°-180° C., weighed 8.5 g (67%). The ir spectrum indicated that the crude product was nearly pure alpha-(2-(2,2-dicyanovinyl)-2-(alpha,alpha,alpha-trifluoro-m-tolyl)hydrazono)malononitrile. A sample of the product (0.5 g) was dissolved in a minimum amount of acetonitrile and the solution put on a column of florasil developed with benzene. The column was eluted with benzene and ether and the combined eluate concentrated at reduced pressure. The yellow residue was washed with benzene until a nearly colorless solid (0.4 g) was obtained. The ir spectrum indicated pure alpha-(2-(2,2-dicyanovinyl)-2-(alpha,alpha,alpha-trifluoro-m-tolyl)hydrazono)malononitrile. An analytical sample, mp 179.5°-181° C., was prepared by recrystallization from benzene; ir (nujol) 3.28 $\mu$ (m), 4.5 $\mu$ (s), 6.2 $\mu$ (s), 6.3 $\mu$ (m), 6.6 $\mu$ (s), 6.65 $\mu$ (s), 6.9 $\mu$ (m), 6.98 $\mu$ (s), 7.6 $\mu$ (s), 8.12 $\mu$ (s), 8.4 $\mu$ (s), 8.55 $\mu$ (s), 8.62 $\mu$ (s), 8.83 $\mu$ (s), 9.15 $\mu$ (s), 9.4 $\mu$ (s), 13.05 $\mu$ (s). Mass spectrum (rel. intensity/fragment) 314 (44, $M^+$), 295 (2, $M^+$—F), 288 (1, $M^+$—CN), 262 (2, $M^+$—2CN), 237 (22, $M^+$—CH=C(CN)$_2$), 236 (47, $M^+$—N=C(CN)$_2$, 216 (71, $CF_3C_6H_4NCH$=(CN)$_2$—HF), 209 (39, $CF_3C_6H_4NCH$=C(CN)$_2$—HCN), 172 (30, $CF_3C_6H_4N^+$=CH), 167 (19, $CF_3C_6H_4N^+CH$=C(CN)$_2$—CF$_3$), 159 (9, $CF_3C_6H_4N^+$), 145 (100, $CF_3C_6H_4^+$); nmr (D$_6$—DMSO) $\delta$8.0 (m, 3, Ar$\underline{H}$), $\delta$8.2 (s, 1, Ar$\underline{H}$), $\delta$8.75 (s, H, —NC$\underline{H}$=C(CN)$_2$).

Calc'd. for $C_{14}H_5F_3N_6$: C, 53.50; H, 1.61; N, 26.75. Found: C, 53.52; H, 1.68; N, 26.72.

The benzene washes were concentrated at reduced pressure and 0.05 g of bright yellow solid, mp 150° (d), recovered. The product was recrystallized from hexane; ir (nujol) 3.08 $\mu$ (m), 3.15 $\mu$ (w), 3.22 $\mu$ (w), 4.5 $\mu$ (s), 6.15 $\mu$ (w), 6.22 $\mu$ (m), 6.38 $\mu$ (s), 6.72 $\mu$ (s), 6.82 $\mu$ (s), 7.5 $\mu$ (s), 7.7 $\mu$ (s), 7.82 $\mu$ (s), 8.5 $\mu$ (s), 8.8 $\mu$ (s), 9.4 $\mu$ (s), 11.22 $\mu$ (s), 12.52 $\mu$ (s), 14.1-14.5 $\mu$ (s). Mass spectrum rel. intensity/fragment) 238 (31, $M^+$), 219 (5, $M^+$—F), 211 (1, $M^+$—HCN), 173 (5, $M^+$—CH(CN)$_2$), 160 (7, M+—N=C(CN)$_2$), 159 (14, CF$_3$C$_6$H$_4$N+), 145 (100, CF$_3$C$_6$H$_4$+). The data indicate that the by-product is 2-(alpha,alpha,alpha-trifluoro-m-tolyl)hydrazonomalononitrile. The remaining 8 g of crude product was purified in the same manner to yield 6.5 g of alpha-(2-(2,2-dicyanovinyl)-2-(alpha,alpha,alpha-trifluoro-m-tolyl)hydrazono)malononitrile and 0.7 g of by-product 2-(alpha,alpha,alpha-trifluoro-m-tolyl)hydrazonomalononitrile.

EXAMPLE 5

Reaction of 3,4-Dichlorophenyl Sydnone with TCNE

A mixture of 4.6 g of (0.02 mol) of 3,4-dichlorophenyl sydnone (mp 149°–150° (d), 2.8 g (0.022 mol) of TCNE and 50 ml of o-dichlorobenzene was heated at the reflux temperature under nitrogen for 7 hours. Some TCNE sublimed into the condenser during the heating period. The black solution was diluted with petroleum ether and the gummy black precipitate stored under ether overnight. The dark brown powder which formed under the ether was collected and washed with ether. The air-dried product, mp 153°–157°, weighed 3.5 g. An additional quantity of crude product (0.5 g) was recovered from the combined filtrates for a total yield of 4.0 g (63%). Attempts to purify the crude product by chromatography on forasil resulted in extensive hydrolysis. Purification was achieved by decolorization with activated carbon. A mixture of 1 g of crude product, 1.5 g of decolorizing charcoal and 35 ml of benzene was boiled for 1-2 minutes and then filtered. The residue was extracted with 15 ml of hot benzene and the combined filtrate concentrated at reduced pressure. The residue was washed with ether to yield 0.8 g of pure alpha-(2-(2,2-dicyanovinyl)-2-(3,4-dichlorophenyl)hydrazono)malononitrile, mp 162.5°–164°. An analytical sample, mp 162.5°–164.5°, was prepared by recrystallization from benzene; ir (nujol) 3.28 μ (m), 4.5 μ (s), 6.22 μ (s), 6.38 μ (m), 6.6 μ (s), 6.9 μ (s), 7.42 μ (s), 8.2 μ (s), 8.6 μ (s), 8.88 μ (s), 13.0 μ (s).

Calc'd. for C$_{13}$H$_4$Cl$_2$N$_6$: C, 49.54; H, 1.28; N, 26.67. Found: C, 49.64; H, 1.30; N, 26.60.

When crude alpha-(2-(2,2-dicyanovinyl)-2-(3,4-dichlorophenyl)hydrazono)malononitrile was chromatographed on florasil, the benzene eluate contained 2-(3,4-dichlorophenyl)hydrazonomalononitrile, mp 188°, as a major product; ir (nujol) 3.08 μ (m), 3.12 μ (w), 3.22 μ (w), 4.5 μ (s), 6.32 μ (s), 6.6 μ (s), 6.92 μ (s), 7.9 μ (s), 8.05 μ (s), 8.22 μ (s), 12.3 μ (s), 14.7 μ (s).

EXAMPLE 6

Reaction of 3-Fluorophenyl Sydnone with TCNE

In accordance with the procedure described in Example 1, 3-fluorophenyl sydnone was reacted with TCNE yielding alpha-(2-(2,2-dicyanovinyl)-2-(3-fluorophenyl)hydrazono)malononitrile in 55% yield. The purified product had a mp 133.5°–135° C.

Calc'd.: C, 59.09; H, 1.91; N, 31.81. Found: C, 59.13; H, 1.79; N, 31.88.

EXAMPLE 7

Reaction of 4-Chlorophenyl Sydnone with TCNE

In accordance with the procedure described in Example 1, 4-chlorophenyl sydnone was reacted with TCNE yielding alpha-(2-(2,2-dicyanovinyl)-2-(4-chlorophenyl)hydrazono)malononitrile in 35% yield. The purified product had a mp 161°–162° C.

Calc'd.: C, 55.63; H, 1.80; N, 29.64. Found: C, 55.54; H, 1.85; N, 29.90.

EXAMPLE 8

Reaction of 3-Chlorophenyl Sydnone with TCNE

In accordance with the procedure described in Example 1, 3-chlorophenyl sydnone was reacted with TCNE yielding alpha-(2-(2,2-dicyanovinyl)-2-(3-chlorophenyl)hydrazono)malononitrile in 33% yield. The purified product had a mp 113°–115° C.

Calc'd.: C, 55.63; H, 1.80; N, 29.94. Found: C, 55.53; H, 1.89; N, 29.91.

EXAMPLE 9

Reaction of 3-Tolyl Sydnone with TCNE

In accordance with the procedure described in Example 1, 3-tolyl sydnone was reacted with TCNE yielding alpha-(2-(2,2-dicyanovinyl)-2-(3-tolyl)hydrazono)malononitrile in 41% yield. The purified product had a mp 157°–159° C.

Calc'd.: C, 64.61; H, 3.10. Found: C, 64.57; H, 3.15.

EXAMPLE 10

Reaction of 2,4-Difluorophenyl Sydnone with TCNE

In accordance with the procedure described in Example 1, 2,4-difluorophenyl sydnone was reacted with TCNE yielding alpha(2-(2,2-dicyanovinyl)-2-(2,4-difluorophenyl)hydrazono)-malononitrile in 32% yield. The purified product had a mp 140°–142° C.

Calc'd.: C, 55.33; H, 1.43; N, 29.78. Found: C, 55.10; H, 1.46; N, 29.60.

EXAMPLE 11

Reaction of 4-Fluorophenyl Sydnone with TCNE

In accordance with the procedure described in Example 1, 4-fluorophenyl sydnone was reacted with TCNE yielding alpha-(2-(2,2-dicyanovinyl)-2-(4-fluorophenyl)hydrazono)malononitrile in 52% yield. The purified product had a mp 138°–139° C.

Calc'd.: C, 59.09; H, 1.91; N, 31.81. Found: C, 58.98; H, 1.98; N, 31.96.

EXAMPLE 12

Reaction of 4-Methoxyphenyl Sydnone with TCNE

In accordance with the procedure described in Example 1, 4-methoxyphenyl sydnone was reacted with TCNE yielding alpha-(2-(2,2-dicyanovinyl)-2-(4-methoxyphenyl)hydrazono)malononitrile in 58% yield. The purified product had a mp 143°–145° C.

Calc'd.: C, 60.87; H, 2.92; N, 30.42. Found: C, 60.88; H, 2.92; N, 30.50.

EXAMPLE 13

Reaction of p-Tolyl Sydnone with TCNE

In accordance with the procedure described in Example 1, p-tolyl sydnone was reacted with TCNE yielding alpha-(2-(2,2-dicyanovinyl)-2-(p-tolyl)hydrazono)-malononitrile in 52% yield. The purified product had a mp 168°–169° C.

Calc'd.: C, 64.61; H, 3.10 Found: C, 64.55; H, 3.14.

EXAMPLE 14

Reaction of 3,4-Dimethylphenyl Sydnone with TCNE

In accordance with the procedure described in Example 1, 3,4-dimethylphenyl sydnone was reacted with TCNE yielding alpha-(2-(2,2-dicyanovinyl)-2-(3,4-dimethylphenyl)hydrazono)malononitrile in 56% yield. The purified product had a mp 162°–163° C.

Calc'd.: C, 65.68; H, 3.67. Found: C, 65.63; H, 3.72.

EXAMPLE 15

Reaction of p-Thiomethylphenyl Sydnone with TCNE

In accordance with the procedure described in Example 1, p-thiomethylphenyl sydnone was reacted with TCNE yielding alpha-(2-(2,2-dicyanovinyl)-2-(p-thiomethylphenyl)hydrazono)malononitrile in 44% yield. The purified product had a mp 164°–165° C.

Calc'd.: C, 57.52; H, 2.72; N, 28.75. Found: C, 57.74; H, 2.82; N, 28.56.

EXAMPLE 16

Reaction of 4-Bromophenyl Sydnone with TCNE

In accordance with the procedure described in Example 1, 4-bromophenyl sydnone was reacted with TCNE yielding alpha-(2-(2,2-dicyanovinyl)-2-(4-bromophenyl)hydrazono)malononitrile in 50% yield. The purified product had a mp 191°–192° C.

Calc'd.: C, 48.02; H, 1.55; N, 25.85. Found: C, 47.95; H, 1.58; N, 25.93.

EXAMPLE 17

Reaction of 3,5-Bis(Trifluoromethylphenyl) Sydnone with TCNE

In accordance with the procedure described in Example 1, 3,5-bis(trifluoromethylphenyl) sydnone was reacted with TCNE yielding alpha-(2,2-dicyanovinyl)-2-(3,5-bis(trifluoromethylphenyl)hydrazono)malononitrile in 23% yield. The purified product had a mp 166°–167° C.

Calc'd.: C, 47.13; H, 1.05; N, 21.99. Found: C, 47.28; H, 1.13; N, 21.77.

EXAMPLE 18

Reaction of p-Cyanophenyl Sydnone with TCNE

In accordance with the procedure described in Example 1, p-cyanophenyl sydnone was reacted with TCNE yielding alpha-(2-(2,2-dicyanovinyl)-2-(p-cyanophenyl)hydrazono)malononitrile in 29.4% yield. The purified product had a mp 231° C.

Calc'd.: C, 61.99; H, 1.86. Found: C, 61.89; H, 1.89.

EXAMPLE 19

Reaction of 4-Chloro-Alpha,Alpha,Alpha-Trifluoro-m-Tolyl Sydnone with TCNE

In accordance with the procedure described in Example 1, 4-chloro-alpha,alpha,alpha-trifluoro-m-tolyl sydnone was reacted with TCNE yielding alpha-(2-(2,2-dicyanovinyl)-2-(4-chloro-alpha,alpha,alpha-trifluoro-m-tolyl)hydrazono)malononitrile in 57.4% yield. The purified product had a mp 148°–150° C. Spectral data was consistent with the assigned structure.

EXAMPLE 20

Reaction of 3-Chloro-4-Fluorophenyl Sydnone with TCNE

In accordance with the procedure described in Example 1, 3-chloro-4-fluorophenyl sydnone was reacted with TCNE yielding alpha-(2-(2,2-dicyanovinyl)-2-(3-chloro-4-fluorophenyl)hydrazono)malononitrile in 40% yield. The purified product had a mp 80°–82° C. Spectral data was consistent with the assigned structure.

EXAMPLE 21

The post-emergence herbicidal activity of various compounds of this invention is demonstrated as follows. The active ingredients are applied in spray form to 14–21 day-old specimens of various plant species. The spray, a water or organic solvent-water solution containing active ingredient and a surfactant (35 parts butylamine salt of dodecylbenzenesulfonic acid and 65 parts tall oil condensed with ethylene oxide in the ratio of 11 moles ethylene oxide to 1 mole tall oil), is applied to the plants in different sets of pans at several rates (kg per hectare) of active ingredient. The treated plants are placed in a greenhouse and the effects are observed and recorded after approximately 2 weeks or approximately 4 weeks. The data is given in Tables I and II.

The post-emergence herbicidal activity index used in Tables I and II is as follows:

| Plant Response | Index |
|---|---|
| 0–24% Injury | 0 |
| 25–49% Injury | 1 |
| 50–74% Injury | 2 |
| 75–99% Injury | 3 |
| All Killed | 4 |
| Species not present at time of treatment | 5 |

In said Tables, WAT indicates weeks after treatment, and the plant species treated are each represented by a code letter as follows:

| | |
|---|---|
| A - Canada Thistle | K - Barnyard Grass |
| B - Cocklebur | L - Soybean |
| C - Velvet Leaf | M - Sugar Beet |
| D - Morning Glory | N - Wheat |
| E - Lambsquarters | O - Rice |
| F - Smartweed | P - Sorghum |
| G - Nutsedge | Q - Wild Buckwheat |
| H - Quackgrass | R - Hemp Sesbania |
| I - Johnson Grass | S - Panicum Spp |
| J - Downy Brome | T - Crabgrass |

TABLE I

| Compound | WAT | kg/h | A | B | C | D | E | F | G | H | I | J | K |
|---|---|---|---|---|---|---|---|---|---|---|---|---|---|
| 1 | 2 | 11.2 | 0 | 4 | 1 | 1 | 4 | 4 | 0 | 1 | 0 | 1 | 2 |
|   | 4 | 11.2 | 0 | 4 | 1 | 1 | 4 | 4 | 0 | 0 | 0 | 0 | 1 |
|   | 2 | 5.6 | 0 | 3 | 1 | 1 | 4 | 4 | 0 | 1 | 0 | 1 | 3 |
|   | 4 | 5.6 | 0 | 3 | 1 | 1 | 4 | 4 | 0 | 0 | 0 | 0 | 2 |
| 2 | 2 | 11.2 | 1 | 3 | 2 | 2 | 4 | 2 | 0 | 0 | 1 | 1 | 0 |
|   | 4 | 11.2 | 0 | 4 | 2 | 1 | 4 | 3 | 0 | 0 | 0 | 1 | 0 |
|   | 2 | 5.6 | 2 | 2 | 1 | 1 | 4 | 2 | 0 | 0 | 0 | 0 | 0 |
|   | 4 | 5.6 | 2 | 2 | 1 | 1 | 4 | 2 | 0 | 0 | 0 | 0 | 1 |
| 3 | 2 | 11.2 | 1 | 4 | 3 | 3 | 4 | 2 | 0 | 0 | 0 | 0 | 2 |
|   | 2 | 4.48 | 2 | 3 | 2 | 2 | 4 | 0 | 0 | 0 | 0 | 1 | 2 |
| 4 | 2 | 11.2 | 4 | 4 | 4 | 2 | 4 | 5 | 0 | 0 | 1 | 1 | 2 |
|   | 2 | 4.48 | 4 | 3 | 2 | 2 | 4 | 5 | 1 | 0 | 0 | 0 | 2 |
| 5 | 2 | 11.2 | 1 | 2 | 3 | 2 | 4 | 3 | 0 | 1 | 0 | 2 | 2 |

TABLE I-continued

| Compound | WAT | kg/h | A | B | C | D | E | F | G | H | I | J | K |
|---|---|---|---|---|---|---|---|---|---|---|---|---|---|
|   | 2 | 4.48 | 4 | 2 | 1 | 1 | 4 | 4 | 0 | 0 | 0 | 0 | 1 |
| 6 | 2 | 11.2 | 4 | 3 | 3 | 3 | 4 | 4 | 2 | 1 | 0 | 0 | 1 |
|   | 4 | 11.2 | 4 | 4 | 3 | 3 | 4 | 4 | 2 | 1 | 0 | 0 | 0 |
|   | 2 | 5.6 | 3 | 4 | 4 | 3 | 4 | 4 | 0 | 0 | 0 | 1 | 2 |
|   | 4 | 5.6 | 4 | 4 | 4 | 4 | 4 | 4 | 0 | 0 | 0 | 1 | 1 |
| 7 | 2 | 11.2 | 4 | 3 | 2 | 2 | 4 | 4 | 1 | 0 | 0 | 0 | 0 |
|   | 4 | 11.2 | 4 | 3 | 2 | 1 | 4 | 4 | 1 | 0 | 0 | 0 | 0 |
|   | 2 | 5.6 | 4 | 3 | 2 | 1 | 4 | 4 | 1 | 0 | 0 | 0 | 3 |
|   | 4 | 5.6 | 4 | 4 | 2 | 1 | 4 | 4 | 0 | 0 | 0 | 0 | 3 |
| 8 | 2 | 11.2 | 3 | 3 | 3 | 2 | 3 | 3 | 0 | 1 | 0 | 2 | 3 |
|   | 4 | 11.2 | 2 | 4 | 4 | 2 | 4 | 3 | 0 | 2 | 0 | 2 | 2 |
|   | 2 | 5.6 | 3 | 3 | 3 | 2 | 3 | 3 | 1 | 0 | 3 | 1 | 1 |
|   | 4 | 5.6 | 4 | 4 | 3 | 1 | 4 | 4 | 0 | 0 | 4 | 1 | 1 |
| 9 | 2 | 11.2 | 2 | 3 | 3 | 1 | 4 | 4 | 0 | 0 | 0 | 1 | 1 |
|   | 4 | 11.2 | 1 | 4 | 4 | 1 | 4 | 4 | 0 | 0 | 0 | 1 | 1 |
|   | 2 | 5.6 | 1 | 2 | 3 | 0 | 4 | 4 | 0 | 0 | 1 | 1 | 1 |
|   | 4 | 5.6 | 1 | 1 | 3 | 1 | 4 | 4 | 0 | 0 | 0 | 0 | 1 |
| 10 | 2 | 11.2 | 1 | 4 | 4 | 2 | 4 | 4 | 0 | 1 | 0 | 1 | 2 |
|   | 4 | 11.2 | 1 | 4 | 4 | 2 | 4 | 4 | 0 | 1 | 1 | 1 | 3 |
|   | 2 | 5.6 | 1 | 3 | 2 | 2 | 4 | 3 | 0 | 0 | 0 | 0 | 2 |
|   | 4 | 5.6 | 1 | 3 | 2 | 1 | 4 | 3 | 0 | 0 | 1 | 0 | 3 |
| 11 | 2 | 11.2 | 1 | 4 | 4 | 3 | 4 | 4 | 1 | 2 | 4 | 1 | 3 |
|   | 4 | 11.2 | 1 | 4 | 4 | 3 | 4 | 4 | 0 | 2 | 4 | 1 | 4 |
|   | 2 | 5.6 | 1 | 4 | 4 | 2 | 4 | 4 | 0 | 0 | 0 | 0 | 3 |
|   | 4 | 5.6 | 1 | 4 | 4 | 1 | 4 | 4 | 0 | 1 | 1 | 1 | 3 |
| 12 | 2 | 11.2 | 1 | 2 | 2 | 2 | 4 | 4 | 0 | 0 | 1 | 0 | 2 |
|   | 4 | 11.2 | 1 | 2 | 2 | 2 | 4 | 4 | 0 | 1 | 1 | 0 | 2 |
|   | 2 | 5.6 | 0 | 2 | 1 | 1 | 2 | 2 | 0 | 0 | 0 | 0 | 3 |
|   | 4 | 5.6 | 0 | 2 | 0 | 1 | 2 | 2 | 0 | 0 | 0 | 0 | 3 |
| 13 | 2 | 11.2 | 0 | 2 | 1 | 1 | 4 | 4 | 0 | 0 | 0 | 1 | 1 |
|   | 4 | 11.2 | 1 | 1 | 1 | 1 | 4 | 4 | 0 | 0 | 0 | 0 | 0 |
|   | 2 | 5.6 | 0 | 1 | 0 | 1 | 4 | 1 | 0 | 0 | 0 | 0 | 3 |
|   | 4 | 5.6 | 1 | 1 | 0 | 0 | 4 | 1 | 0 | 0 | 0 | 0 | 2 |
| 14 | 2 | 11.2 | 0 | 1 | 0 | 1 | 3 | 0 | 0 | 0 | 1 | 0 | 0 |
|   | 2 | 5.6 | 0 | 0 | 0 | 0 | 3 | 0 | 0 | 0 | 0 | 0 | 0 |
| 15 | 2 | 11.2 | 2 | 1 | 1 | 1 | 4 | 4 | 0 | 0 | 0 | 0 | 2 |
|   | 4 | 11.2 | 2 | 1 | 1 | 1 | 4 | 4 | 0 | 0 | 0 | 0 | 2 |
|   | 2 | 5.6 | 1 | 1 | 0 | 1 | 4 | 4 | 0 | 0 | 0 | 0 | 2 |
|   | 4 | 5.6 | 1 | 1 | 0 | 1 | 4 | 4 | 0 | 0 | 0 | 0 | 2 |
| 16 | 2 | 11.2 | 1 | 3 | 3 | 3 | 3 | 3 | 1 | 1 | 1 | 2 | 3 |
|   | 4 | 11.2 | 1 | 4 | 4 | 2 | 4 | 4 | 0 | 0 | 0 | 1 | 3 |
|   | 2 | 5.6 | 1 | 3 | 3 | 1 | 3 | 3 | 1 | 2 | 1 | 1 | 3 |
|   | 4 | 5.6 | 0 | 4 | 4 | 0 | 4 | 4 | 0 | 3 | 0 | 0 | 4 |
| 17 | 2 | 11.2 | 4 | 4 | 4 | 1 | 4 | 4 | 1 | 0 | 0 | 1 | 3 |
|   | 2 | 5.6 | 5 | 2 | 3 | 2 | 4 | 4 | 0 | 1 | 0 | 2 | 4 |
| 18 | 2 | 11.2 | 3 | 4 | 2 | 1 | 4 | 4 | 0 | 0 | 1 | 1 | 3 |
|   | 2 | 5.6 | 0 | 0 | 0 | 0 | 3 | 2 | 0 | 0 | 0 | 0 | 1 |
| 19 | 2 | 11.2 | 2 | 1 | 2 | 2 | 3 | 3 | 2 | 1 | 1 | 1 | 3 |
|   | 4 | 11.2 | 2 | 1 | 2 | 2 | 3 | 3 | 2 | 1 | 1 | 1 | 2 |
| 20 | 2 | 11.2 | 2 | 3 | 3 | 1 | 4 | 4 | 1 | 1 | 1 | 0 | 3 |
|   | 4 | 11.2 | 1 | 3 | 3 | 2 | 4 | 4 | 1 | 1 | 1 | 0 | 2 |

TABLE II

| Compound | WAT | kg/h | L | M | N | O | P | B | Q | D | R | E | F | C | J | S | K | T |
|---|---|---|---|---|---|---|---|---|---|---|---|---|---|---|---|---|---|---|
| 1 | 2 | 1.12 | 1 | 1 | 0 | 1 | 1 | 1 | 4 | 1 | 2 | 2 | 2 | 0 | 0 | 1 | 2 | 2 |
|   | 2 | 0.28 | 1 | 0 | 0 | 0 | 1 | 1 | 1 | 0 | 1 | 1 | 0 | 0 | 0 | 0 | 0 | 0 |
| 2 | 2 | 5.6 | 3 | 4 | 1 | 1 | 2 | 3 | 1 | 2 | 4 | 4 | 4 | 3 | 1 | 2 | 2 | 1 |
|   | 4 | 5.6 | 3 | 4 | 1 | 1 | 2 | 3 | 1 | 1 | 4 | 4 | 4 | 4 | 0 | 1 | 2 | 1 |
|   | 2 | 1.12 | 2 | 1 | 1 | 0 | 1 | 2 | 0 | 1 | 2 | 3 | 1 | 1 | 0 | 0 | 0 | 1 |
|   | 2 | 0.28 | 1 | 0 | 1 | 0 | 0 | 1 | 0 | 1 | 1 | 1 | 0 | 1 | 0 | 0 | 1 | 0 |
| 3 | 2 | 4.48 | 2 | 2 | 0 | 1 | 2 | 2 | 4 | 3 | 3 | 4 | 3 | 3 | 1 | 4 | 3 | 3 |
|   | 2 | 1.12 | 2 | 1 | 0 | 0 | 0 | 1 | 0 | 2 | 2 | 4 | 0 | 0 | 0 | 0 | 1 | 2 |
| 4 | 2 | 4.48 | 0 | 0 | 0 | 0 | 0 | 0 | 0 | 0 | 0 | 3 | 5 | 4 | 0 | 0 | 0 | 0 |
|   | 2 | 1.12 | 2 | 2 | 1 | 0 | 2 | 2 | 2 | 2 | 4 | 4 | 5 | 1 | 1 | 0 | 1 | 2 |
|   | 2 | 1.12 | 0 | 0 | 0 | 0 | 0 | 0 | 0 | 0 | 0 | 0 | 5 | 4 | 0 | 0 | 0 | 0 |
|   | 2 | 0.56 | 1 | 1 | 0 | 0 | 2 | 1 | 0 | 1 | 1 | 4 | 5 | 1 | 0 | 0 | 0 | 2 |
| 5 | 2 | 4.48 | 3 | 4 | 3 | 1 | 3 | 2 | 4 | 3 | 4 | 4 | 4 | 4 | 2 | 3 | 4 | 4 |
|   | 2 | 1.12 | 2 | 4 | 1 | 1 | 2 | 3 | 2 | 3 | 3 | 4 | 4 | 1 | 1 | 3 | 3 | 2 |
| 6 | 2 | 5.6 | 3 | 4 | 1 | 3 | 1 | 4 | 4 | 2 | 4 | 4 | 4 | 3 | 1 | 1 | 3 | 4 |
|   | 4 | 5.6 | 3 | 4 | 2 | 3 | 1 | 4 | 4 | 1 | 4 | 4 | 4 | 2 | 1 | 1 | 3 | 4 |
|   | 2 | 1.12 | 1 | 2 | 1 | 2 | 1 | 2 | 1 | 0 | 2 | 4 | 4 | 1 | 1 | 0 | 0 | 3 |
|   | 4 | 1.12 | 1 | 2 | 1 | 2 | 1 | 0 | 1 | 1 | 1 | 4 | 4 | 0 | 0 | 0 | 0 | 1 |
| 7 | 2 | 5.6 | 3 | 4 | 1 | 2 | 1 | 4 | 4 | 3 | 4 | 4 | 4 | 4 | 4 | 1 | 2 | 2 |
|   | 4 | 5.6 | 3 | 4 | 1 | 1 | 1 | 4 | 4 | 4 | 4 | 4 | 4 | 4 | 4 | 1 | 2 | 2 |
|   | 2 | 1.12 | 2 | 3 | 0 | 0 | 0 | 3 | 4 | 1 | 3 | 3 | 4 | 3 | 3 | 0 | 2 | 1 |
|   | 4 | 1.12 | 2 | 4 | 0 | 0 | 0 | 4 | 4 | 0 | 3 | 4 | 4 | 4 | 2 | 0 | 2 | 0 |
| 8 | 2 | 5.6 | 2 | 4 | 1 | 1 | 2 | 3 | 4 | 1 | 4 | 4 | 4 | 4 | 2 | 1 | 1 | 0 |
|   | 4 | 5.6 | 2 | 4 | 0 | 0 | 2 | 3 | 4 | 1 | 4 | 4 | 4 | 4 | 3 | 2 | 1 | 0 |
|   | 2 | 1.12 | 1 | 4 | 1 | 1 | 1 | 3 | 4 | 3 | 4 | 4 | 3 | 3 | 1 | 1 | 2 | 1 |
|   | 4 | 1.12 | 1 | 4 | 0 | 0 | 0 | 4 | 4 | 4 | 4 | 4 | 4 | 3 | 2 | 1 | 2 | 0 |
| 9 | 2 | 5.6 | 3 | 4 | 2 | 1 | 4 | 3 | 4 | 2 | 4 | 4 | 4 | 4 | 3 | 2 | 3 | 3 |
|   | 4 | 5.6 | 3 | 4 | 2 | 1 | 4 | 4 | 4 | 2 | 4 | 4 | 4 | 4 | 3 | 2 | 3 | 3 |
|   | 2 | 1.12 | 1 | 2 | 1 | 0 | 2 | 1 | 1 | 1 | 2 | 2 | 2 | 3 | 1 | 1 | 1 | 1 |
|   | 4 | 1.12 | 1 | 2 | 1 | 0 | 2 | 1 | 0 | 1 | 1 | 2 | 2 | 1 | 1 | 1 | 1 | 1 |
| 10 | 2 | 5.6 | 3 | 4 | 0 | 1 | 0 | 4 | 0 | 1 | 4 | 4 | 4 | 0 | 1 | 1 | 1 | 1 |
|   | 4 | 5.6 | 3 | 4 | 0 | 2 | 1 | 4 | 0 | 1 | 4 | 4 | 4 | 0 | 1 | 1 | 1 | 0 |
|   | 2 | 1.12 | 2 | 2 | 0 | 1 | 0 | 2 | 0 | 1 | 2 | 4 | 3 | 0 | 1 | 0 | 0 | 1 |

TABLE II-continued

| Compound | WAT | kg/h | L | M | N | O | P | B | Q | D | R | E | F | C | J | S | K | T |
|---|---|---|---|---|---|---|---|---|---|---|---|---|---|---|---|---|---|---|
|  | 4 | 1.12 | 1 | 2 | 0 | 1 | 1 | 3 | 0 | 1 | 1 | 4 | 3 | 2 | 0 | 1 | 0 | 1 |
| 11 | 2 | 5.6 | 3 | 2 | 1 | 0 | 1 | 1 | 0 | 2 | 4 | 4 | 4 | 3 | 0 | 0 | 1 | 1 |
|  | 4 | 5.6 | 2 | 2 | 1 | 0 | 2 | 1 | 0 | 1 | 4 | 4 | 4 | 4 | 0 | 0 | 1 | 1 |
|  | 2 | 1.12 | 1 | 1 | 0 | 0 | 0 | 1 | 0 | 0 | 2 | 2 | 2 | 2 | 0 | 0 | 0 | 1 |
|  | 4 | 1.12 | 1 | 0 | 0 | 0 | 0 | 0 | 0 | 0 | 1 | 1 | 1 | 1 | 0 | 0 | 0 | 1 |
| 12 | 2 | 5.6 | 1 | 1 | 1 | 1 | 2 | 1 | 0 | 1 | 1 | 4 | 3 | 2 | 0 | 0 | 1 | 1 |
|  | 4 | 5.6 | 1 | 1 | 1 | 1 | 2 | 0 | 0 | 1 | 1 | 4 | 3 | 1 | 0 | 0 | 0 | 0 |
|  | 2 | 1.12 | 1 | 0 | 0 | 1 | 1 | 0 | 0 | 0 | 0 | 1 | 1 | 0 | 0 | 0 | 0 | 0 |
| 13 | 2 | 5.6 | 2 | 4 | 1 | 1 | 1 | 3 | 3 | 1 | 4 | 4 | 4 | 2 | 0 | 1 | 1 | 2 |
|  | 4 | 5.6 | 2 | 4 | 1 | 0 | 0 | 3 | 4 | 2 | 4 | 4 | 4 | 2 | 0 | 1 | 1 | 2 |
|  | 2 | 1.12 | 1 | 1 | 1 | 0 | 1 | 1 | 1 | 0 | 2 | 2 | 1 | 0 | 0 | 0 | 0 | 0 |
| 14 |  |  |  |  |  |  |  | Not tested |  |  |  |  |  |  |  |  |  |  |
| 15 | 2 | 5.6 | 1 | 3 | 1 | 0 | 2 | 1 | 3 | 1 | 4 | 4 | 4 | 2 | 0 | 1 | 3 | 3 |
|  | 4 | 5.6 | 1 | 4 | 1 | 1 | 3 | 1 | 3 | 1 | 4 | 4 | 4 | 2 | 0 | 1 | 3 | 4 |
|  | 2 | 1.12 | 1 | 1 | 0 | 0 | 1 | 0 | 0 | 1 | 1 | 4 | 1 | 0 | 0 | 0 | 1 | 1 |
| 16 | 2 | 5.6 | 2 | 4 | 1 | 1 | 1 | 3 | 4 | 2 | 4 | 4 | 4 | 4 | 0 | 2 | 2 | 3 |
|  | 2 | 1.12 | 2 | 3 | 0 | 1 | 1 | 0 | 0 | 1 | 4 | 4 | 4 | 0 | 0 | 0 | 1 | 1 |
|  | 4 | 1.12 | 1 | 3 | 0 | 0 | 1 | 0 | 0 | 1 | 4 | 4 | 4 | 0 | 0 | 0 | 1 | 1 |
|  | 2 | 0.28 | 1 | 0 | 0 | 0 | 1 | 0 | 0 | 1 | 2 | 3 | 3 | 0 | 0 | 0 | 0 | 1 |
|  | 4 | 0.28 | 1 | 0 | 0 | 0 | 1 | 0 | 0 | 0 | 1 | 4 | 4 | 0 | 0 | 0 | 0 | 1 |
| 17 | 2 | 5.6 | 2 | 4 | 2 | 1 | 2 | 2 | 4 | 2 | 4 | 4 | 4 | 4 | 1 | 3 | 3 | 3 |
|  | 4 | 5.6 | 2 | 4 | 1 | 1 | 2 | 2 | 4 | 1 | 4 | 4 | 4 | 4 | 1 | 3 | 3 | 3 |
|  | 2 | 1.12 | 1 | 4 | 1 | 0 | 1 | 0 | 0 | 0 | 1 | 4 | 4 | 1 | 0 | 1 | 1 | 1 |
|  | 2 | 0.28 | 0 | 0 | 0 | 0 | 0 | 0 | 0 | 0 | 0 | 1 | 1 | 0 | 0 | 0 | 0 | 0 |
| 18 | 2 | 5.6 | 1 | 3 | 2 | 1 | 2 | 1 | 2 | 1 | 3 | 4 | 4 | 2 | 0 | 1 | 2 | 2 |
|  | 2 | 1.12 | 1 | 1 | 1 | 1 | 2 | 0 | 2 | 1 | 2 | 3 | 2 | 1 | 0 | 1 | 2 | 2 |
|  | 2 | 0.28 | 1 | 0 | 0 | 0 | 1 | 0 | 0 | 1 | 1 | 2 | 2 | 0 | 0 | 0 | 0 | 1 |
| 19 | 2 | 5.6 | 2 | 4 | 3 | 3 | 3 | 1 | 4 | 1 | 3 | 4 | 4 | 4 | 3 | 3 | 2 | 4 |
|  | 2 | 1.12 | 1 | 1 | 0 | 0 | 2 | 0 | 0 | 0 | 2 | 3 | 2 | 1 | 1 | 0 | 1 | 2 |
| 20 | 2 | 5.6 | 2 | 4 | 3 | 1 | 3 | 3 | 4 | 2 | 4 | 4 | 4 | 3 | 2 | 1 | 4 | 3 |
|  | 2 | 1.12 | 1 | 3 | 1 | 0 | 1 | 1 | 0 | 0 | 1 | 4 | 4 | 1 | 0 | 0 | 2 | 2 |
|  | 2 | 1.12 | 1 | 4 | 0 | 0 | 0 | 1 | 0 | 0 | 1 | 4 | 4 | 1 | 0 | 0 | 1 | 1 |
|  | 2 | 0.28 | 1 | 1 | 0 | 0 | 0 | 0 | 0 | 0 | 0 | 1 | 0 | 0 | 0 | 0 | 1 | 0 |

EXAMPLE 22

The pre-emergent herbicidal activity of various compounds of this invention is demonstrated as follows. A good grade of top soil is placed in aluminum pans and compacted to a depth of ⅜ to ½ inch from the top of each pan. A predetermined number of seeds or vegetative propagules of each of several plant species are placed on top of the soil in each pan and then pressed down. Herbicidal compositions (as described in Example 21) employing the active ingredients of this invention are applied by admixture with or incorporation in the top layer of soil.

In this method, the soil required to cover the seeds and propagules is weighed and admixed with a herbicidal composition containing a known amount of active ingredient. The pans are then filled with the admixture and leveled. Watering is carried out by permitting the soil in the pans to absorb moisture through apertures in the pan bottoms. The seed and propagule containing pans are placed on a wet sand bench and maintained for approximately 2 weeks under ordinary conditions of sunlight and watering. At the end of this period the number of emerged plants of each species is noted and compared to an untreated control. The data is given in Table III.

The pre-emergent herbicidal activity index used below is based upon the average percent control of each species as follows:

| Percent Control | Index |
|---|---|
| 0 – 25% | 0 |
| 26 – 50% | 1 |
| 51 – 75% | 2 |
| 76 – 100% | 3 |

Plant species are identified in Table III by the same code letters used in Example 21.

TABLE III

| Compound | WAT | kg/h | Plant Species Screening Test A | | | | | | | | | | | Plant Species Screening Test B | | | | | |
|---|---|---|---|---|---|---|---|---|---|---|---|---|---|---|---|---|---|---|---|
|  |  |  | A | B | C | D | E | F | G | H | I | J | K | L | M | N | O | P | B |
| 5 | 2 | 11.2 | 1 | 0 | 1 | 0 | 3 | 2 | 1 | 0 | 0 | 1 | 1 | 0 | 3 | 0 | 0 | 0 | 0 |
| 7 | 2 | 11.2 | 0 | 0 | 0 | 0 | 3 | 0 | 0 | 0 | 0 | 1 | 0 |  |  |  |  |  |  |
| 8 | 2 | 11.2 | 0 | 0 | 0 | 0 | 3 | 0 | 0 | 0 | 0 | 1 | 0 |  |  |  |  |  |  |
| 16 | 2 | 11.2 | 3 | 1 | 1 | 5 | 3 | 3 | 1 | 0 | 1 | 3 | 2 |  |  |  |  |  |  |
|  | 2 | 11.2 | 1 | 0 | 1 | 0 | 3 | 3 | 0 | 0 | 0 | 2 | 0 |  |  |  |  |  |  |
| 17 | 2 | 11.2 | 1 | 3 | 1 | 1 | 3 | 3 | 1 | 0 | 0 | 3 | 1 |  |  |  |  |  |  |
|  | 2 | 5.6 |  |  |  |  |  |  |  |  |  |  |  | 1 | 3 | 0 | 0 | 0 | 0 |
|  | 2 | 1.12 |  |  |  |  |  |  |  |  |  |  |  | 0 | 3 | 0 | 0 | 0 | 0 |
| 19 | 2 | 11.2 | 0 | 0 | 3 | 1 | 3 | 3 | 0 | 0 | 0 | 2 | 0 |  |  |  |  |  |  |
|  | 2 | 5.6 |  |  |  |  |  |  |  |  |  |  |  | 0 | 1 | 0 | 1 | 0 | 0 |
| 20 |  |  |  |  |  |  |  |  |  |  |  |  |  |  |  |  |  |  |  |

| Compound | WAT | kg/h | Plant Species Screening Test B | | | | | | | | |
|---|---|---|---|---|---|---|---|---|---|---|---|
|  |  |  | Q | D | R | E | F | C | J | S | K | T |
| 5 | 2 | 11.2 | 0 | 0 | 3 | 3 | 2 | 3 | 0 | 1 | 2 | 0 |
| 7 | 2 | 11.2 |  |  |  |  |  |  |  |  |  |  |
| 8 | 2 | 11.2 |  |  |  |  |  |  |  |  |  |  |
| 16 | 2 | 11.2 |  |  |  |  |  |  |  |  |  |  |
|  | 2 | 11.2 |  |  |  |  |  |  |  |  |  |  |
| 17 | 2 | 11.2 |  |  |  |  |  |  |  |  |  |  |
|  | 2 | 5.6 | 0 | 1 | 1 | 3 | 2 | 1 | 1 | 0 | 2 | 0 |

TABLE III-continued

|    | 2 | 1.12 | 0 | 0 | 0 | 0 | 0 | 0 | 0 | 0 | 0 | 0 |
| 19 | 2 | 11.2 |   |   |   |   |   |   |   |   |   |   |
|    | 2 | 5.6  | 0 | 1 | 0 | 1 | 0 | 0 | 0 | 0 | 0 | 0 |
| 20 |   |      |   |   |   |   |   |   |   |   |   |   |

From the test results presented in Tables I and II, it can be seen that the post-emergent herbicidal activity of the compounds of this invention is, for the most part, selectivity against broadleaf plants and relative safety for grasses. Of particular interest is the unique activity of many of the compounds on weeds of the Malvaceae family, e.g. velvetleaf. On the other hand, the test results showing pre-emergent herbicidal activity (Table III) clearly show the selectivity of action on Cocklebur and a few other species. In this regard it should be recognized that each individual species selected for the above tests is a representative member of a recognized family of plant species.

The herbicidal compositions, including concentrates which require dilution prior to application to the plants, of this invention contain from 5 to 95 parts by weight of at least one active ingredient and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, all parts being by weight of the total composition. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these. From the viewpoint of economy and convenience, water is the preferred diluent.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alchols, amines or acid amides, long chain acid esters of sodium isothionate, esters of sodium sulfosuccinate, sulfated or sulfonated fatty acid esters, petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acid) taurates.

Water dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The water-dispersible powder of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform and usually contains from 5 to about 95 parts by weight active ingredient, from about 0.25 to 25 parts by weight dispersant, and from about 4.5 to 94.5 parts by weight of water.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. The emulsifiable oil compositions generally contain from about 5 to 95 parts active ingredient, about 1 to 50 parts surface active agent and about 4 to 94 parts solvent, all parts being by weight based on the total weight of emulsifiable oil.

Although compositions of this invention can also contain other additaments, for example, fertilizers, phytotoxicants and plant growth regulators, pesticides and the like used as adjuvants or in combination with any of the above-described adjuvants, it is preferred to employ the compositions of this invention alone with sequential treatments with the other phytotoxicants, fertilizers and the like for maximum effect. For example, the field could be sprayed with a composition of this invention either before or after being treated with fertilizers, other phytotoxicants and the like. The compositions of this invention can also be admixed with the other materials, e.g., fertilizers, other phytotoxicants, etc., and applied in a single application. Chemicals useful in combination with the active ingredients of this invention either simultaneously or sequentially include, for example, triazines, ureas, carbamates, acetamides, acetanilides, uracils, acetic acids, phenols, thiolcarbamates, triazoles, benzoic acids, nitriles and the like.

Fertilizers useful in combination with the active ingredients include, for example, ammonium nitrate, urea, potash, and superphosphate.

When operating in accordance with the present invention, effective amounts of the malononitriles are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds of this invention to the plant is essential and critical for the practice of the present invention. The exact amount of active ingredient to be employed is dependent upon the response desired in the plant as well as such other factors as the plant species and stage of development thereof, and the amount of rainfall as well as the specific malononitrile employed. In foliar treatment for the control of vegetative growth, the active ingredients are applied in amounts from about 0.112 to about 22.4 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although the invention is described with respect to specific modifications, the details thereof are not to be construed as limitations except to the extent indicated in the following claims.

What is claimed is:

1. A dicyanovinylhydrazonomalononitrile having the formula

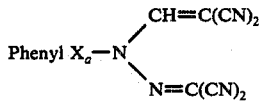

wherein each X is a substituent on said Phenyl selected from halogen, alkyl of 1 to 8 carbon atoms, alkoxy or alkylthio or haloalkyl of 1 to 8 carbon atoms, cyano and nitro and wherein $a$ is an integer from 0 to 5.

2. A dicyanovinylhydrazonomalononitrile according to claim 1 wherein X is alkyl.

3. A dicyanovinylhydrazonomalononitrile according to claim 1 wherein X is halogen.

4. A dicyanovinylhydrazonomalononitrile according to claim 1 wherein X is haloalkyl.

5. A dicyanovinylhydrazonomalononitrile according to claim 1 wherein X is the thioalkyl.

6. Alpha-(2-(2,2-dicyanovinyl)-2-phenyl hydrazono)-malononitrile, according to claim 1.

7. Alpha-(2-(2,2-dicyanovinyl)-2-(3,4-dichlorophenyl)hydrazono)malononitrile, according to claim 1.

8. Alpha-(2-(2,2-dicyanovinyl)-2-(3-fluorophenyl)hydrazono)malononitrile, according to claim 1.

9. Alpha-(2-(2,2-dicyanovinyl)-2-(4-chlorophenyl)hydrazono)malononitrile, according to claim 1.

10. Alpha-(2-(2,2-dicyanovinyl)-2-(3-chlorophenyl)-hydrazono)malononitrile, according to claim 1.

11. Alpha-(2-(2,2-dicyanovinyl)-2-(3-tolyl)hydrazono)malononitrile, according to claim 1.

12. Alpha-(2-(2,2-dicyanovinyl)-2-(2,4-difluorophenyl)hydrazono)malononitrile, according to claim 1.

13. Alpha-(2-(2,2-dicyanovinyl)-2-(4-fluorophenyl)-hydrazono)malononitrile, according to claim 1.

14. Alpha-(2-(2,2-dicyanovinyl)-2-(4-methoxyphenyl)hydrazono)malononitrile, according to claim 1.

15. Alpha-(2-(2,2-dicyanovinyl)-2-(2-ethylphenyl)hydrazono)malononitrile, according to claim 1.

16. Alpha-(2-(2,2-dicyanovinyl)-2-(p-tolyl)hydrazono)malononitrile, according to claim 1.

17. Alpha-(2-(2,2-dicyanovinyl)-2-(3,4-dimethylphenyl)-hydrazono)malononitrile, according to claim 1.

18. Alpha-(2-(2,2-dicyanovinyl)-2-(p-thiomethylphenyl)hydrazono)malononitrile, according to claim 1.

19. Alpha-(2-(2,2-dicyanovinyl)-2-(4-bromophenyl)-hydrazono)malononitrile, according to claim 1.

20. Alpha-(2-(2,2-dicyanovinyl)-2-(4-nitrophenyl)hydrazono)malononitrile, according to claim 1.

21. Alpha-(2-(2,2-dicyanovinyl)-2-(3,5-bis(trifluoromethylphenyl)hydrazono)malononitrile, according to claim 1.

22. Alpha-(2-(2,2-dicyanovinyl)-2-(p-cyanophenyl)-hydrazono)malononitrile, according to claim 1.

23. Alpha-(2-(2,2-dicyanovinyl)-2-(4-chloro-alpha,alpha,alpha-trifluoro-m-tolyl)hydrazono)malononitrile, according to claim 1.

24. Alpha-(2-(2,2-dicyanovinyl)-2-(3-trifluorotolyl)-hydrazono)malononitrile, according to claim 1.

25. Process for preparing a dicyanovinylhydrazonomalononitrile having the formula

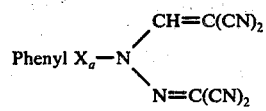

wherein each X is a substituent on said Phenyl selected from halogen, alkyl of 1 to 8 carbon atoms, alkoxy or alkylthio or haloalkyl of 1 to 8 carbon atoms, cyano and nitro and wherein $a$ is an integer from 0 to 5 which comprises forming a reaction mixture of tetracyanoethylene and a sydnone having the formula

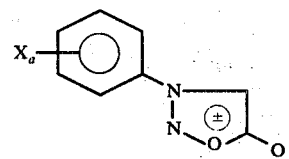

wherein X and $a$ are as above defined, heating said reaction mixture in the presence of an inert solvent to a reaction temperature of from 160° to 185° C. whereby said dicyanovinylhydrazonomalononitrile is produced.

26. Process according to claim 25 wherein the sydnone is phenyl sydnone.

27. Process according to claim 25 wherein the sydnone is 3-trifluoromethylphenyl sydnone.

28. Process according to claim 25 wherein the sydnone is 3,4-dichlorophenyl sydnone.

29. Process according to claim 25 wherein the sydnone is p-nitrophenyl sydnone.

30. Process according to claim 25 wherein the sydnone is o-ethylphenyl sydnone.

31. Process according to claim 25 wherein the sydnone is 3-fluorophenyl sydnone.

32. Process according to claim 25 wherein the sydnone is 4-chlorophenyl sydnone.

33. Process according to claim 25 wherein the sydnone is 2,4-difluorophenyl sydnone.

34. Process according to claim 25 wherein the sydnone is 4-fluorophenyl sydnone.

35. Process according to claim 25 wherein the sydnone is 4-bromophenyl sydnone.

36. Process according to claim 25 wherein the sydnone is 3,5-bis(trifluoromethylphenyl) sydnone.

37. Process according to claim 25 wherein the sydnone is p-cyanophenyl sydnone.

38. Process according to claim 25 wherein the sydnone is 1,3,5-trifluoro, 2-methyl, 4-chlorophenyl sydnone.

39. Process according to claim 25 wherein the sydnone is 3-trifluoromethylphenyl sydnone.

40. Process according to claim 25 wherein the inert solvent is o-dichlorobenzene.

41. A herbicidal method which comprises contacting a plant with a herbicidally effective amount of a dicyanovinylhydrazonomalononitrile of the formula

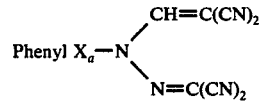

wherein each X is a substituent on said Phenyl selected from halogen, alkyl of 1 to 8 carbon atoms, alkoxy or alkylthio or haloalkyl of 1 to 8 carbon atoms, cyano and nitro and wherein $a$ is an integer from 0 to 5.

42. A herbicidal method according to claim 41 wherein the dicyanovinylhydrazonomalononitrile is alpha-(2-(2,2-dicyanovinyl)-2-(3-fluorophenyl)hydrazono)malononitrile.

43. A herbicidal method according to claim 41 wherein the dicyanovinylhydrazonomalononitrile is alpha-(2-(2,2-dicyanovinyl)-2-(4-chlorophenyl)hydrazono)malononitrile.

44. A herbicidal method according to claim 41 wherein the dicyanovinylhydrazonomalononitrile is alpha-(2-(2,2-dicyanovinyl)-2-(2,4-difluorophenyl)hydrazono)malononitrile.

45. A herbicidal method according to claim 41 wherein the dicyanovinylhydrazonomalononitrile is alpha-(2-(2,2-dicyanovinyl)-2-(4-fluorophenyl)hydrazono)malononitrile.

46. A herbicidal method according to claim 41 wherein the dicyanovinylhydrazonomalononitrile is alpha-(2-(2,2-dicyanovinyl)-2-(4-bromophenyl)hydrazono)malononitrile.

47. A herbicidal method according to claim 41 wherein the dicyanovinylhydrazonomalononitrile is alpha-(2-(2,2-dicyanovinyl)-2-(3,5-bis(trifluoromethylphenyl)hydrazono)malononitrile.

48. A herbicidal method according to claim 41 wherein the dicyanovinylhydrazonomalononitrile is alpha-(2-(2,2-dicyanovinyl)-2-(p-cyanophenyl)hydrazono)malononitrile.

49. A herbicidal method according to claim 41 wherein the dicyanovinylhydrazonomalononitrile is alpha-(2-(2,2-dicyanovinyl)-2-(4-chloro-alpha,alpha,alpha-trifluoro-m-tolyl)hydrazono)malononitrile.

50. A herbicidal method according to claim 41 wherein the dicyanovinylhydrazonomalononitrile is alpha-(2-(2,2-dicyanovinyl)-2-(3-trifluorotolyl)hydrazono)malononitrile.

51. A phytotoxic composition comprising an inert adjuvant and an effective amount of a compound of the formula

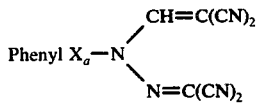

wherein each X is a substituent on said Phenyl selected from halogen, alkyl of 1 to 8 carbon atoms, alkoxy or alkylthio or haloalkyl of 1 to 8 carbon atoms, cyano and nitro and wherein $a$ is an integer from 0 to 5.

52. A composition in accordance with claim 51 wherein X is halogen and $a$ is an integer from 0 to 3.

53. A composition in accordance with claim 51 wherein X is haloalkyl and $a$ is an integer from 1 to 2.

54. A composition in accordance with claim 51 wherein X is alkyl and $a$ is an integer from 1 to 2.

55. A composition in accordance with claim 51 wherein X is cyano and $a$ is 1.

56. A composition in accordance with claim 51 wherein the malononitrile is alpha-(2-(2,2-dicyanovinyl)-2-(4-chlorophenyl)hydrazono)malononitrile.

57. A composition in accordance with claim 51 wherein the malononitrile is alpha-(2-(2,2-dicyanovinyl)-2-(3,4-dichlorophenyl)hydrazono)-malononitrile.

58. A composition in accordance with claim 51 wherein the malononitrile is alpha-(2-(2,2-dicyanovinyl)-2-(3-chlorophenyl)hydrazono)malononitrile.

59. A composition in accordance with claim 51 wherein the malononitrile is alpha-(2-(2,2-dicyanovinyl)-2-(4-chloro-alpha,alpha,alpha-trifluoro-m-tolyl)hydrazono)malononitrile.

* * * * *